(12) United States Patent
Löf

(10) Patent No.: US 11,167,150 B2
(45) Date of Patent: Nov. 9, 2021

(54) SELECTION OF RADIOTHERAPY TREATMENT PLANS

(71) Applicant: RaySearch Laboratories AB, Stockholm (SE)

(72) Inventor: Johan Löf, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 639 days.

(21) Appl. No.: 14/903,192

(22) PCT Filed: Dec. 20, 2013

(86) PCT No.: PCT/EP2013/077729
§ 371 (c)(1),
(2) Date: Jan. 6, 2016

(87) PCT Pub. No.: WO2015/090457
PCT Pub. Date: Jun. 25, 2015

(65) Prior Publication Data
US 2016/0144198 A1    May 26, 2016

(51) Int. Cl.
*G16H 40/20* (2018.01)
*G16H 20/40* (2018.01)
*A61N 5/10* (2006.01)
*G16H 70/20* (2018.01)

(52) U.S. Cl.
CPC ............ *A61N 5/103* (2013.01); *G16H 40/20* (2018.01); *G16H 20/40* (2018.01); *G16H 70/20* (2018.01)

(58) Field of Classification Search
USPC .......................................................... 705/2, 3
See application file for complete search history.

(56) References Cited

U.S. PATENT DOCUMENTS

| | | | | |
|---|---|---|---|---|
| 2007/0129967 A1* | 6/2007 | Thompson | ......... | G06Q 10/1095 705/2 |
| 2010/0208867 A1* | 8/2010 | Nord | ....... | A61N 5/103 378/65 |
| 2010/0303205 A1* | 12/2010 | Kapoor | ................ | A61B 6/4458 378/65 |
| 2012/0016690 A1* | 1/2012 | Ramarajan | ............ | G06F 19/345 705/2 |
| 2015/0095044 A1* | 4/2015 | Hartman | ................ | G16H 50/20 705/2 |

FOREIGN PATENT DOCUMENTS

WO    WO-2010/094777 A1    8/2010

OTHER PUBLICATIONS

"Integer Programming", published on Wikipedia on Dec. 12, 2012. (Year: 2012).*

(Continued)

*Primary Examiner* — Joshua B Blanchette
(74) *Attorney, Agent, or Firm* — Faegre Drinker Biddle & Reath LLP

(57) ABSTRACT

A method for automatic selection of a treatment plan for a patient is provided, where the automatic selection is at least partly based on the plan quality and required resources for each treatment plan in relation to the availability of resources.

7 Claims, 2 Drawing Sheets

(56) References Cited

OTHER PUBLICATIONS

John M. Harrold and Roberts. Parker, "Clinically relevant cancer chemotherapy dose scheduling via mixed-integer optimization", Computers and Chemical Engineering 33 (2009) 2042-2054. (Year: 2009).*

Saure, "Dynamic multi-appointment patient scheduling for radiation therapy", European Journal of Operational Research vol. 223, Issue 2, Dec. 1, 2012, pp. 573-584. (Year: 2012).*

Legrain, "Stochastic optimization of the scheduling of a radiotherapy center," Journal of Physics: Conference Series 616 (2015) 012008 (Year: 2015).*

International Search Report dated Sep. 10, 2014 in International Application No. PCT/EP2013/077729.

\* cited by examiner

SELECTION OF RADIOTHERAPY TREATMENT PLANS

CROSS REFERENCE TO RELATED APPLICATION

This application is a § 371 National Stage Application of PCT International Application No. PCT/EP2013/077729 filed Dec. 20, 2013, the entire contents of which is incorporated by reference herein in its entirety.

FIELD OF THE INVENTION

The present invention relates to radiotherapy, and in particular to selection of a radiotherapy treatment plan for a patient.

BACKGROUND

Scheduling in general, and scheduling of radiotherapy treatments in particular, is a well-known, and in some regards a complex, problem. A large radiotherapy clinic can utilize a plurality of treatment machines, and a large number of patients could be treated every day. In such facilities, manual scheduling of the treatments can often become complicated. Computer-aided scheduling, i.e. employing computer programs which are specifically designed for the purpose, are sometimes used for achieving efficient scheduling of radiotherapy treatment. Such computer-aided scheduling might use various algorithms for scheduling a plurality of treatment sessions within the clinic as efficient as possible. The scheduling could comprise consideration of various parameters, such as the duration of the planned treatment, condition of the patients being scheduled for treatment, and so on.

A treatment plan, defining the parameters to be used when treating a patient, is usually determined a long time, sometimes many weeks, before the actual treatment. The treatment plan is often determined on the basis of an internal image of the patient, such as a computer tomography (CT) scan, and specifies treatment parameters, such as, for example, a treatment technique, a treatment modality and beam parameters (e.g. number, angles of incidence, shapes, intensities, etc., of radiation beams to be delivered). The determined parameters and the treatment plan thus defined will in some regards be specific for the type of machine used for delivering the treatment. The clinical goals of a treatment, for example in terms of specified levels of minimum radiation dose delivered to a target (such as a tumor) and maximum allowed dose to various organs at risk (OARs), are usually defined by a radiation oncologist. Then, a treatment planner determines a treatment plan in order to fulfill these goals and obtain a treatment plan which produces a dose distribution which, as far as possible, treats the target while sparing normal tissue. Usually, a treatment planning system is used for determining the treatment plan. In inverse treatment planning an optimization algorithm is employed for finding a set of treatment parameters that will generate a dose distribution within the subject that most closely matches the desired dose. A treatment planner sometimes creates multiple alternative plans, based on the same treatment modality and technique, or based on some other available treatment modality or treatment technique. The treatment planner and/or the radiation oncologist might then choose the best candidate of the alternative treatment plans. The reason for determining multiple treatment plans to choose from could be that it is often difficult to foresee in advance which kind of treatment plan will be most effective for a specific case.

Radiotherapy treatment is usually fractionated, i.e. the treatment time is extended, often over several weeks, where fractions of the total planned dose are administered daily. Hence, when a treatment plan has been determined, a plurality of treatment sessions in accordance with the treatment plan will be scheduled, either manually or (semi-) automatically using computer-aided scheduling.

The processes according to the prior art for determining and scheduling treatment plans do not provide for an efficient usage of the treatment machines or other available resources at a clinic.

An aim of the present invention is to overcome, or at least mitigate, these drawbacks, and in particular to enable improved utilization of one or more resources used in connection with radiotherapy treatment.

SUMMARY

According to one aspect of the invention, a method is provided for automatic selection of a radiotherapy treatment plan for a patient, from a set of treatment plans comprising at least two alternative radiotherapy treatment plans for the patient. Preferably, the automatic selection, performed in a processor, is based on at least:
- the plan quality of each of said at least two alternative radiotherapy treatment plans;
- the resources required for treatment according to each of said at least two alternative radiotherapy treatment plans; and
- the availability of said resources.

According to another aspect of the invention, a computer program product is provided. Preferably, the computer program product comprises computer-readable instructions which, when executed on a computer, will cause the computer to perform the method for automatic selection of a radiotherapy treatment plan for a patient.

According to yet another aspect of the invention, a computer system is provided. Preferably, the computer system comprises a processor coupled to at least one memory having stored thereon a computer program comprising computer-readable instructions for automatic selection of a radiotherapy treatment plan for a patient, wherein the processor is configured to execute the computer-readable instructions.

Hence, the invention achieves the aim defined above by automatically selecting, for each patient, a treatment plan from a set of alternative treatment plans which is optimal with respect to both treatment of the patient and usage of resources, e.g. treatment machines, in view of the availability of said resources in a clinic. Accordingly, when alternative candidate treatment plans are available for a patient, an automatic selection of a plan is performed not only based on plan quality in relation to required resources but also in relation to resource availability at the time being. Consequently, a treatment plan which requires lots of resources can be automatically selected in times where resource availability is high, and rejected in times when resource availability is low. The latter situation would generally require a thorough analysis of which patients have the greatest benefit of "advanced" treatments requiring some specific resources. However, according to the present invention, the most appropriate treatment plan for a patient will always be selected in accordance with current circumstances.

According to some embodiments, one or more of said at least two alternative radiotherapy treatment plans is an automatically determined treatment plan determined on the basis of a planned dose of another of said alternative radiotherapy treatment plans. Thereby, a plurality of alternative treatment plans can easily be determined using a minimum of manual work.

According to some embodiments, the plan selection comprises an optimization process wherein a combined plan quality for a plurality of alternative radiotherapy treatment plans for a plurality of patients is optimized subject to constraints that resources required for delivering treatment according to selected radiotherapy treatment plans may not exceed resource availability. Thereby, a total plan quality for a group of patients could be optimized and treatment plans for all the patients selected simultaneously.

According to some embodiments, at least one or more of said at least two alternative radiotherapy treatment plans is a combined plan based on a combination of two different radiotherapy treatment plans, wherein the plan quality of said combined plan is based on a combination of the plan qualities of said two different radiotherapy treatment plans. Hence, a combination of different treatment techniques and/or modalities which is optimal in view of the available resources will be determined for a patient.

According to some embodiments, plan selection is partly based on a shortest possible time till delivery of treatment according to each of the at least two alternative radiotherapy treatment plans. Thereby, treatment plans for which the corresponding required resources indicate that treatment can be commenced without delay could be favored in the plan selection process. This might be advantageous since it often is beneficial to commence treatment as quick as possible.

According to some embodiments, plan selection is partly based on a patient priority reflecting the urgency for treatment of a patient. Thereby, treatment plans for which the corresponding required resources indicate that treatment can be commenced without delay could be favored primarily for the patients for which treatment is deemed to be most urgent.

According to some embodiments, radiotherapy treatment corresponding to a selected treatment plan for at least one patient is scheduled.

Further aspects of the invention will become apparent by consideration of the detailed description and accompanying drawings. These are only for purposes of illustrating preferred embodiments and are not to be construed as limiting the invention.

DETAILED DESCRIPTION

Figure 1:
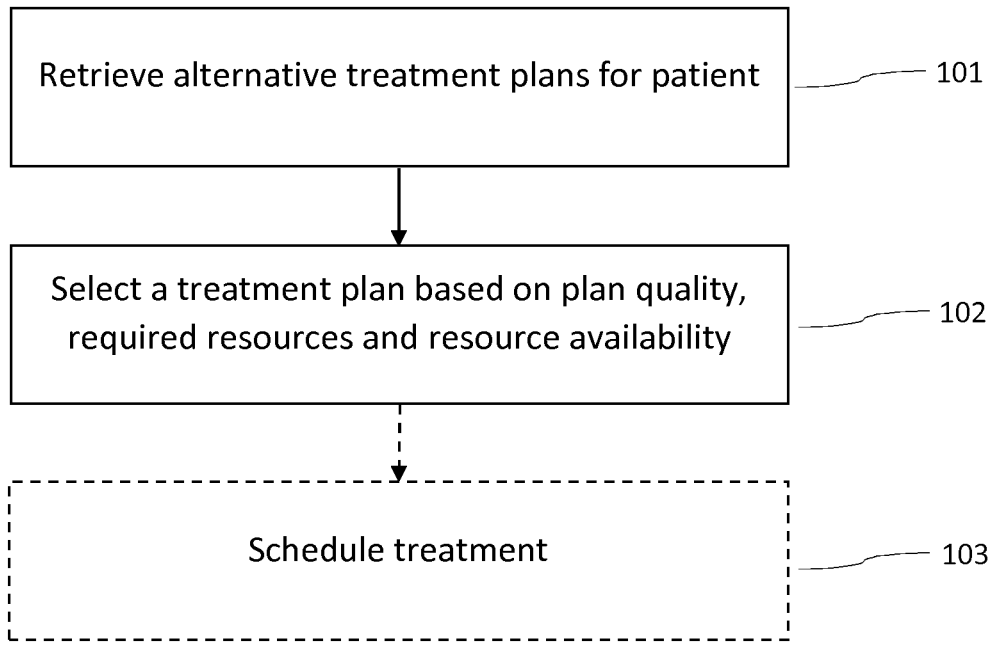
FIG. 1 is a flowchart of a method according to the invention.

FIG. 1 is a flowchart showing the different steps of a method according to the invention.

In step 101, at least two alternative candidate treatment plans are retrieved. The candidate plans are different from each other at least according to some aspect. The plans could differ regarding treatment modality, for example, either using photons (X-rays), protons, electrons or any other treatment modality. Alternatively or additionally, treatment plans could be based on mixtures of different modalities, such that, for example, a part of a treatment is conducted using photons and another part using protons or electrons. As another example, the plans could differ regarding the treatment techniques used. Various different treatment techniques are known in the art. These are not necessarily machine specific but can often be delivered using the same kind of treatment machine.

Examples of treatment techniques applicable when using photon-based treatment are three-dimensional conformal radiation therapy (3D-CRT), or various kinds of intensity modulated radiation therapy (IMRT). Treatment beams from different directions can be delivered to the patient where the cross section of a beam could be modified using a multi-leaf collimator (MLC). In IMRT, the intensity distribution of a specific beam can be modulated, for example using a plurality of different MLC apertures administrated in sequence, or by using a sliding window technique. Another treatment technique is volumetrically modulated arc therapy (VMAT) which employs a constant rotation along an arc during which the beam is always on and the MLC aperture is changing continuously. Another example of arc therapy is helical tomotherapy, where radiation is delivered slice-by-slice using a fan beam and a binary MLC collimator for modulating the beam. Examples of proton treatment techniques are active scanning, where a proton pencil beam is scanned over a plurality of "spots" in the target, and passive scattering, where a scatterer is used for extending the dose laterally. These and other treatment techniques are well-known in the art and do not require any further explanation here.

In step 102, a plan is selected on the basis of the qualities of the plans and the resources required for treatment in accordance with the plans, in view of the availability of said resources.

A measure for plan quality can be determined in many different ways. The plan quality is at least based on a dosimetric quality, e.g. relating to dose levels in different structures, target dose conformity or homogeneity, total dose delivered to patient, etc. It is possible to also incorporate a biological effect of the dose according to the treatment modality used. Thereby, as an example, when comparing a photon plan and a proton plan, the increased biological effect of protons will be taken into consideration when determining the plan quality of the proton plan. Also other parameters could affect the plan quality, which will be discussed in more detail below. In general, though, a treatment time is not included in the calculation of a plan quality since this parameter rather relates to resource usage, and is considered in view of resource availability, as described in more detail below. However, in order to obtain a meaningful plan selection, all candidate plans should preferably have been optimized (or at least efforts been made for doing so) with respect to treatment time, so that all candidate plans are as time efficient as possible in view of the treatment technique being used and the obtained plan quality.

As one example, the plan quality could be based on the degree of fulfillment of clinical goals of the treatment, where the clinical goals for example are defined by an oncologist. According to one example, only treatment plans satisfying a predefined set of important clinical goals are considered as candidate plans. Then, a measure of plan quality for a treatment plan depends on the fulfillment of further clinical goals. The further clinical goals could be categorized according to importance, and satisfying a certain clinical goal could result in an improved plan quality score according to the importance of the clinical goal. Some further dosimetric measure could also influence the plan quality, e.g. for differentiating treatment plans satisfying the same number of clinical goals. For example, the average dose to the patient (which preferably should be as low as possible) could affect the plan quality score.

According to some example embodiments, plan qualities are normalized with respect to the "best" plan (e.g., referring to the example above, the plan with lowest average dose among the plans satisfying most clinical goals), such that, for example, the best plan for a patient will get a plan quality score of 1, and the plan quality score for the other plans will be the quality relative to the best available plan for the patient. This facilitates comparison of different kinds of treatment plans for different patients. For example, when different measures of plan quality are applied for different patients (e.g. due to different clinical goals), this would facilitate assessment of which patients would benefit most from the more resource-demanding treatments.

As apparent to a person skilled in the art, measures of plan quality could be defined in many other ways on the basis of dosimetric data of treatment plans. One alternative which might be advantageous is to define plan quality based on the estimated biological effect of a delivered dose. For example, plan quality could be based on conventionally used biological models such as normal tissue complication probability (NTCP) models (reflecting the probability of normal tissue complications emerging due to the delivered dose) and/or tumor control probability (TCP) models (reflecting the probability of curing/controlling the tumor). For example, the probability of complication-free tumor cure, sometimes denoted P+, might be a relevant quantity on which a plan quality measure could be based. Such complication-free tumor cure could be defined as the probability of achieving tumor control without causing severe damage to normal tissue, i.e.: $P_+ = TCP*(1-NTCP)$.

Resources, for which required usage and availability are considered, can for example relate to treatment machines, personnel, rooms, equipment, or any other resources required for performing a treatment. As an example, the required time for a treatment, or for quality assurance of a treatment plan, e.g. as estimated manually or automatically based on any relevant parameters of the treatment plan, can be used for defining a measure of required resources. For example, a realistic measure of the time period a treatment machine will be engaged (e.g. including the time required for patient setup, etc.), and which should be used as measure of required resources, could be automatically estimated depending on predetermined criteria, for example relating to the treatment technique used, number of beams, number of segments, number of monitor units (MUs), etc. For some treatment techniques, such as VMAT, the treatment time (i.e. the time for delivering the radiation, not including patient set-up) is well-defined and a measure of required resources can be easily estimated based on this treatment time.

One method for selecting a treatment plan for each of a plurality of patients, in order to provide for optimized resource usage, is to set up an optimization problem where the total plan quality (i.e. the combined plan quality for all selected treatment plans) is optimized, under constraints relating to usage and availability of resources. An example embodiment of such a method is described below with reference to table 1 which illustrates a set of K different patients, each having J alternative treatment plans with plan attributes relating to plan quality (Q), and required resources ($T^{PR}, T^{PH}$).

TABLE 1

| | PATIENT 1 | | | PATIENT 2 | | | ... | PATIENT K | | |
|---|---|---|---|---|---|---|---|---|---|---|
| | Q | $T^{PH}$ | $T^{PR}$ | Q | $T^{PH}$ | $T^{PR}$ | ... | Q | $T^{PH}$ | $T^{PR}$ |
| $P_1$ | $Q_{11}$ | $T_{11}^{PH}$ | $T_{11}^{PR}$ | $Q_{21}$ | $T_{21}^{PH}$ | $T_{21}^{PR}$ | ... | $Q_{K1}$ | $T_{K1}^{PH}$ | $T_{K1}^{PR}$ |
| $P_2$ | $Q_{12}$ | $T_{12}^{PH}$ | $T_{12}^{PR}$ | $Q_{22}$ | $T_{22}^{PH}$ | $T_{22}^{PR}$ | ... | $Q_{K2}$ | $T_{K2}^{PH}$ | $T_{K2}^{PR}$ |
| . | . | . | . | . | . | . | ⋱ | . | . | . |
| . | . | . | . | . | . | . | | . | . | . |
| $P_J$ | $Q_{1J}$ | $T_{1J}^{PH}$ | $T_{1J}^{PR}$ | $Q_{2J}$ | $T_{2J}^{PH}$ | $T_{2J}^{PR}$ | ... | $Q_{KJ}$ | $T_{KJ}^{PH}$ | $T_{KJ}^{PR}$ |

According to this example embodiment, the set of alternative plans for each patient could comprise one or more photon plans, a proton plan and possibly also one or more mixed plans combining proton- and photon therapy. Each of the plans $P_1, P_2, \ldots, P_J$ (a different number of plans may be available for different patients) has a respective plan quality Q and resource usage parameters $T^{PR}$ and $T^{PH}$ corresponding to amounts of time required for proton machine usage and photon machine usage, respectively (see table 1). If no constraints regarding the resource availability would be used, all patients would be scheduled for treatment defined by the treatment plan having the highest plan quality. For example, if for each patient the proton plan has the highest quality, proton therapy would be selected for everyone. If this is not possible, though, a plan selection process according to the invention would find the best possible use of the proton machine by identifying the patients for which an increased amount of proton radiotherapy yield the greatest benefit in comparison to the photon-based radiotherapy treatments. If considering a situation where the k patients are to be scheduled for treatment during a specific time interval in a facility using one proton machine and one conventional linac for photon-based treatment, the availabilities of the machines during the specific time interval dictates a maximum time $T_{max}^{PR}$, available for proton therapy and a maximum time $T_{max}^{PH}$ available for photon therapy. Hence, in this example, the parameters $T_{max}^{PR}$ and $T_{max}^{PH}$ define the resource availability.

The different plans for different patients might be fractionated according to different fractionation schemes, for example using different numbers of fractions. In this example, the parameters $T^{PR}$ and $T^{PH}$ defines the total amount of time of machine usage required for delivering all fractions according to the corresponding treatment plans, and hence, the parameters $T_{max}^{PR}$ and $T_{max}^{PH}$ define the machine availabilities for a time period during which all the treatment sessions for the patients will be scheduled. In alternative embodiments, the parameters $T^{PR}$ and $T^{PH}$ could relate to machine usage for a single treatment session, and the parameters $T_{max}^{PR}$ and $T_{max}^{PH}$ define the machine availabilities during a shorter time period, e.g. a single day.

Assuming that plan quality is defined such that a lower number indicates a better plan, the goal is to minimize the sum of plan qualities (the summands depending on which plan is selected) for all k patients, i.e.:

$$\underset{P}{\text{minimize}} \; f(Q) = \sum_{k} Q(P),$$

subject to the constraints $\Sigma_k T^{PR}(P) < T_{max}^{PR}$ and $\Sigma_k T^{PH}(P) < T_{max}^{PH}$, requiring that the total proton machine usage and photon machine usage can not exceed their respective maximum times available. This will result in a mixed integer problem, which could be solved using various different optimization techniques which are per se known in the art. For example, the problem could be solved using Branch and bound, Cutting-plane methods, Branch and cut, or any other algorithm for solving mixed integer problems. Furthermore, heuristic methods, such as simulated annealing or Tabu search could be employed. These are only examples and other alternatives would be apparent to a person skilled in the art. The invention is thus not limited to the kind of optimization algorithm used for solving the problem.

Moreover, as would also be apparent to the skilled person, if using another definition of plan quality where a higher number indicates a better plan, the optimization would relate to maximizing the total plan quality.

A corresponding approach as described above is applicable also when resource usage requirements and/or resource availability are defined in terms of a plurality of discrete "time slots". A time slot is a short time interval of predefined length. The length of a single time slot preferably corresponds to the time units employed in a scheduling system used for booking appointments, diagnosis, treatments, etc. For example, a predefined length of a single time slot might be five minutes or any other suitable short time interval. An implementation using time slots for representing resource availability and/or required resource usage might in many cases be useful, for example to facilitate scheduling of treatments in accordance with selected treatment plans. Hence, availability might be defined as a number of connected "free" time slots and the required resource usage might be defined in a corresponding way as a required minimum number of connected time slots.

In the simplest case, it is assumed that each machine has a fixed number of available time slots each day and that there are no interruptions in the usage of the machine. Then the constraint is that the sum of the required time slots of the treatment plans delivered with each machine is less than the number of available time slots for that machine.

If there are interruptions in the machine usage during the day, e.g. that machine maintenance is needed or that certain time slots have already been booked, then the available time slots for the machine will be divided into a number of parts of connected time slots. Then there will be one constraint for each part of connected time slots. The constraint for each part of connected time slots is the same as the constraint in the simple case, i.e. the sum of the time slots of the plans delivered during the part of connected time slots must be less than or equal to the number of available connected time slots. A plan selection process according to such an embodiment is further illustrated below with reference to FIGS. 2A and 2B.

A method as described above does not result in treatments actually being scheduled, but might be used to determine the most beneficial set of treatment plans which is possible to schedule during a specified time period. Hence, with reference to FIG. 1, in step 103 a treatment can be scheduled in accordance with the selected treatment plan. As indicated by the dashed lines, this step is optional. The selected treatments could be scheduled in a conventional manner, manually or automatically according to any scheduling technique known in the art. When scheduling treatments, many additional parameters might be taken into consideration, as will be discussed further below.

Figure 2A:
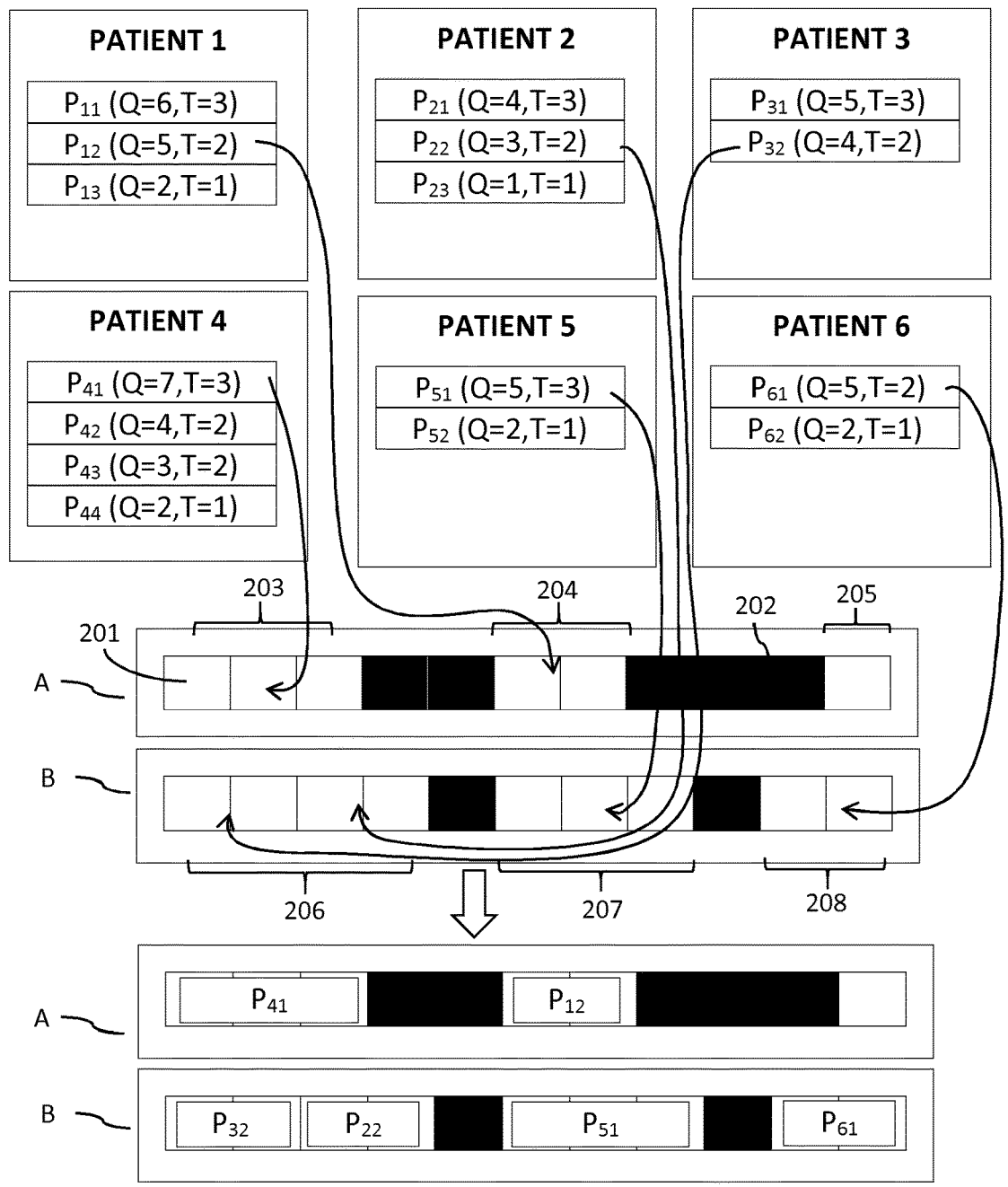
FIG. 2A illustrates the process and the result of treatment plan selection and scheduling for six different patients according to an embodiment of the invention.

FIG. 2A illustrates a treatment plan selection process and scheduling of treatment sessions for six different patients. A corresponding method as described above for selecting treatment plans by optimizing the total plan quality is used. In this example, two similar treatment machines (linear accelerators) A and B are employed for delivering radiation. The treatment machines are illustrated in the figure by their respective schedule for the day during which the treatment sessions for the six patients are to be scheduled. Each schedule is divided into time slots 201. Unavailable time slots 202 are indicated with black color in the schedule. Hence, treatment machine A has three separate parts 203, 204, 205 of connected available time slots (one part 203 with three timeslots, one part 204 with two time slots and one part 205 with one time slot) and treatment machine B also has three separate parts 206, 207, 208 of connected available time slots (one part 206 with 4 slots, one part 207 with three slots and one part 208 with two slots).

Multiple alternative treatment plans, employing different treatment techniques, have been determined for each patient (two plans for each of the $3^{rd}$, $5^{th}$ and $6^{th}$ patient; three plans for each of the first and second patient; and four plans for the $4^{th}$ patient). In this example embodiment, the plan quality is defined such that a higher number indicates a better plan. As an example with reference to patient 4, the plan $P_{41}$ could be an IMRT plan with 11 beams, $P_{42}$ a VMAT plan with dual arcs, plan $P_{43}$ an IMRT plan with 7 beams and $P_{44}$ a single arc VMAT plan. All the plans are considered to be clinically acceptable, although their respective qualities (Q) and time periods (T) required for delivery differ. It is not a requirement that the same kinds of plans are defined for all patients. As indicated in the figure, the alternative plans for the patients require one, two, or three time slots for treatment machine usage. Using an optimization algorithm as described above, where a total plan quality is optimized under constraints that, for each of the parts 203-208 of connected available times slots, the sum of required time slots of selected plans during the respective part of connected time slots must be less than, or equal to, the number of available connected time slots.

The result of such an optimization would be that the plans $P_{12}$, $P_{22}$, $P_{32}$, $P_{41}$, $P_{51}$ and $P_{61}$ are selected for patient 1, patient 2, patient 3, patient 4, patient 5 and patient 6, respectively. This set of treatment plans yields the highest total plan quality ($\Sigma Q=29$) which is possible, in view of the resource availability defined by the number and composition of available time slots. FIG. 2A indicates one possible way of scheduling the selected plans on the two machines A and B.

Figure 2B:
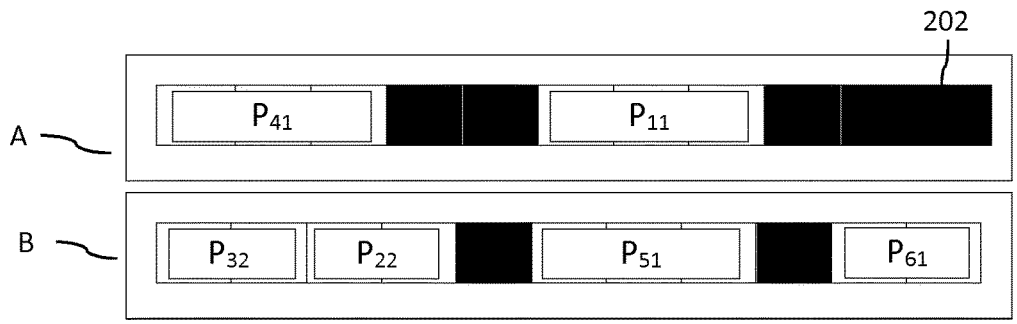
FIG. 2B illustrates the result of a treatment plan selection and scheduling according to an alternative embodiment of the invention.

In an alternative embodiment, assuming that the unavailable time slots 202 represent already scheduled treatments which are possible to reschedule, the improved resource availability would allow for selection of higher quality plans. Optimization with such modified constraints on the resource availability, would result in an optimized total plan quality of (ΣQ=30). FIG. 2B illustrates an example of a scheduled selection of plans according to such embodiment. As indicated in the figure, the unavailable time slots 202 have been rescheduled.

The example described above with reference to FIGS. 2A and 2B, is illustrative and simplified in order to facilitate understanding of the invention. Hence, whereas an optimal solution is easily identified in this example, it is to be understood that a computer implemented optimization process, e.g. as described above, will be required for obtaining an optimal selection of treatment plans according to the invention.

When optimizing a total plan quality, a constraint could be imposed regarding a minimum plan quality. For example, only plans that satisfy a minimum number of relevant clinical goals defined for the treatment are selectable. As another example, a constraint could be imposed on the maximum allowed difference in plan quality between a selected plan and the plan with the greatest plan quality, i.e.: $|Q^{best} - Q^{selected}| < \epsilon$, where $\epsilon$ is a predefined maximum allowed difference in quality between the highest quality plan and the selected plan. Such constraint could be used to ensure that every patient receive treatment which is acceptably close to an optimal treatment. This would also contribute to a result where all compromises in plan quality which are necessary are fairly distributed amongst the patients.

In the examples described above, the resources considered in the optimization relate to treatment machines. However, as also mentioned above, other kinds of resources could be taken into consideration. Hence, if treatment plan selection is limited by availability of other kinds of resources, such as specific personnel, finances, etc., corresponding constraints might be imposed during the plan quality optimization, for example constraints relating to availability of personnel or financial means (e.g. dictating a maximum allowable total cost for the treatments).

Another example of required resource usage which could affect the treatment plan selection relates to quality assurance (QA). A complicated treatment plan, such as an IMRT plan using a large number of beams and segments, requires a substantial QA procedure, requiring availability of the treatment machine as well as competent personnel. Hence, in many cases, the resources needed for QA might be the limiting factor. Therefore, resources required for QA could be considered in a corresponding way when optimizing a total plan quality, by using the resource availability as constraints in accordance with the example embodiments described above.

QA complexity of a plan might also be used to influence the corresponding plan quality used in the optimized plan selection. With such approach, a complex plan requiring an elaborative and time consuming QA procedure could be penalized during optimization. Hence, even if resource availability constraints allow for selecting a treatment plan involving a complex QA procedure, a simpler plan with corresponding dosimetric qualities might be favored since such plan in general is a "better" plan compared to the more complex plan. That is because leakage and various uncertainties (e.g. relating to location and movements of the target, etc.) might have a relatively greater negative effect on the delivered dose for a complex treatment plan, e.g. a plan comprising a large number of segments.

Another parameter which could characterize plan quality, and might be considered in the optimization, is the number of monitor units (MUs) of a treatment. A reduced number of MUs is generally advantageous.

Any other relevant parameter might be incorporated in the process of selecting treatment plans according to the invention. As an example, assuming that it is advantageous to treat a patient as early as possible, the delay of treatment could be used to influence plan selection. Hence, a plan which is possible to schedule with no delay could be favored compared to a plan which is not possible to schedule within the near future. In the following, an example relating to such optimized plan selection and scheduling is described. Assume that two alternative treatment plans are available for a patient. The first plan has a better plan quality $Q_1$ but requires a 30-minute slot for treatment while the second plan has a worse plan quality $Q_2$ but requires only a 20-minute slot. In this example, the plan quality is defined such that a lower number indicates a better plan (i.e., $Q_1 < Q_2$). The resource availability indicates one 20-minute slot available in two days and one 30-minute slot available in six days. According to this example embodiment, a delay weighting factor $W(d)$, dependent on the number of days d that the treatment is delayed, is incorporated into the treatment plan selection process such that a treatment plan is penalized in accordance with the delay for delivering the treatment. Hence, as an example, if $(W(2) \times Q_2) < (W(6) \times Q_1)$, the second plan $Q_2$ would be selected in spite of having worse plan quality.

As a further example, specified patient priorities reflecting treatment urgency for specific patients can be used, favoring selection of treatment plans which can be scheduled without delay for patients which are urgent to treat. Hence, as an example, a delay weighting factor $W(d,P)$ could be a function of both treatment delay d and patient priority P.

In an alternative embodiment relating to scheduling of a plurality of patients having different patient priorities P reflecting treatment urgency, an optimization of total plan quality is performed in accordance with previous embodiments, but where plan quality is weighted by a delay factor $W(d)$ dependent on the treatment delay d of a plan, as described above. As long as the resource availability information comprises information regarding when the resources are available during the time interval for which scheduling is to be performed (and not merely the total time available), the delay factor can be directly derived from the resource availability. After optimization, the patient having the highest priority P is automatically scheduled for treatment according to the selected treatment plan, at the first available opening. Since the delay factors affects the plan selection, the selected treatment plan is likely to define treatment which could be delivered with no or little delay. As a result of scheduling a patient, the resource availability is modified and the delay factors for some plans will change. Accordingly, the optimization process for selecting plans is repeated for the remaining patients, using updated resource availability constraints and correspondingly modified delay factors for affected plans. After the optimization, the next patient in order of priority is scheduled for treatment. This process of alternating optimization and scheduling is repeated until all patients are scheduled. For treatment plans of patients where an early treatment is not crucial (e.g. patients having low priority), a delay factor might not be used, so as to ensure that plan selection is primarily affected by dosimetric quality and not by how soon the treatment can be commenced.

Obviously, this is only one example of how patients could be scheduled according to a varying urgency for treatment. Alternative methods for how to incorporate such parameters in the plan selection process and/or scheduling of treatments are also envisaged.

Determining Candidate Treatment Plans

Each of the alternative treatment plans for a patient could be determined by a treatment planner using a treatment planning system, for example employing inverse treatment planning, as is well-known in the art. Alternatively, some or all of the treatment plans could be determined using an automatic treatment planning method. As an example, for each patient, one treatment plan could be determined "manually" by the treatment planner. Thereafter, alternative treatment plans, using different treatment modalities and/or different treatment techniques, could be automatically determined on the basis of the result of the first treatment plan. This could for example be done by using the dose distribution and/or one or more dose volume histogram (DVH) curves corresponding to the first treatment plan, as treatment objectives. Such optimization is herein referred to as "dose mimicking", indicating that the goal of the optimization is to find a set of treatment parameters which produces a dose distribution which as closely as possible matches or "mimics" a specific dose distribution. For example, first, an IMRT plan using nine equidistant beams could be determined manually. Then, an alternative VMAT plan is automatically calculated by the treatment planning system, using as input the resulting dose distribution of the IMRT plan. Using this approach, a VMAT plan is automatically determined in an optimization process aiming at obtaining the same dose distribution as was obtained for the IMRT plan. A plurality of alternative plans can thus easily be determined using a minimum of manual work.

Dose mimicking could be based on the spatial dose distribution, i.e. using an optimization algorithm wherein the used reference dose objectives are different and specific for each voxel and corresponding to the dose distribution of the reference treatment plan. Alternatively or additionally, dose mimicking could be based on dose volume histograms (DVHs), i.e. using the DVH curves according to the reference treatment plan as planning objectives in the optimization. DVH curves do not comprise any spatial information but are simple 2D representations of the dose distribution in specific structures. Hence, when using DVH-based dose mimicking, the optimization would focus more on the dose-volume statistics and less on the spatial characteristics of the dose distribution. As a further alternative for automatically mimicking a dose distribution, a reference dose fall-off function can be determined from the dose distribution according to the reference treatment plan and used as planning objective. The reference dose fall-off mimicking serves to replicate a characteristic dose fall-off outside a target volume, i.e. how the reference dose depends on the distance to the target.

Mixing Plans with Different Plan Qualities

In the examples above, when analyzing mixed plans involving a combination of different treatment techniques and/or treatment modalities, a plan and a corresponding plan quality is described as determined specifically for each plan. That is, a limited number of alternative plans based on different combinations are analyzed. In alternative embodiments, mixed plans, and their corresponding plan qualities (and required resources), are based on combinations of at least two treatment plans for the patient involving different treatment techniques and/or modalities and having different plan qualities. This will theoretically result in an unlimited number of plans used as basis for the plan selection process. This approach would for example be advantageous when the attributes of a mixed plan, both in terms of plan quality and required resource usage, can be defined as linear combinations of the attributes of the original plans. The process of optimizing a total plan quality, as described previously, could then be easily implemented using any of the optimization approaches exemplified above. As a simple example, assume that an IMRT plan has a greater plan quality compared to an alternative VMAT plan. Both plans deliver the prescribed dose in a corresponding number of fractions. If the VMAT plan is more time-efficient, and if the available time for usage of the treatment machine is limited, a compromise could be defined where some fractions are delivered using the IMRT plan and some fractions are delivered using the VMAT plan. As an illustrative example, assuming that 30 fractions are to be delivered during 6 weeks (one fraction each weekday), the total time available for delivering the treatment during this period is $T_{max}$, an IMRT fraction requires X minutes, and a VMAT fraction requires Y minutes, a maximized plan quality will be achieved if delivering $$\frac{T_{max} - 30Y}{X - Y}$$

fractions of IMRT and the remaining fractions with VMAT.

Constraining Plan Quality

According to the example embodiments described above, a total plan quality is optimized under constraints relating to resource availability. As an alternative, constraints could be imposed on the minimum acceptable plan quality, and some other parameter optimized instead, such as usage of resources. Using this approach, the treatment efficiency is maximized while still assuring a sufficient treatment quality for all patients. Hence, this would result in a maximum amount of resources being available at all times. As one example, the total economic cost of all radiotherapy treatments at a clinic could be minimized while still providing for a sufficiently high treatment quality.

Figure 3:
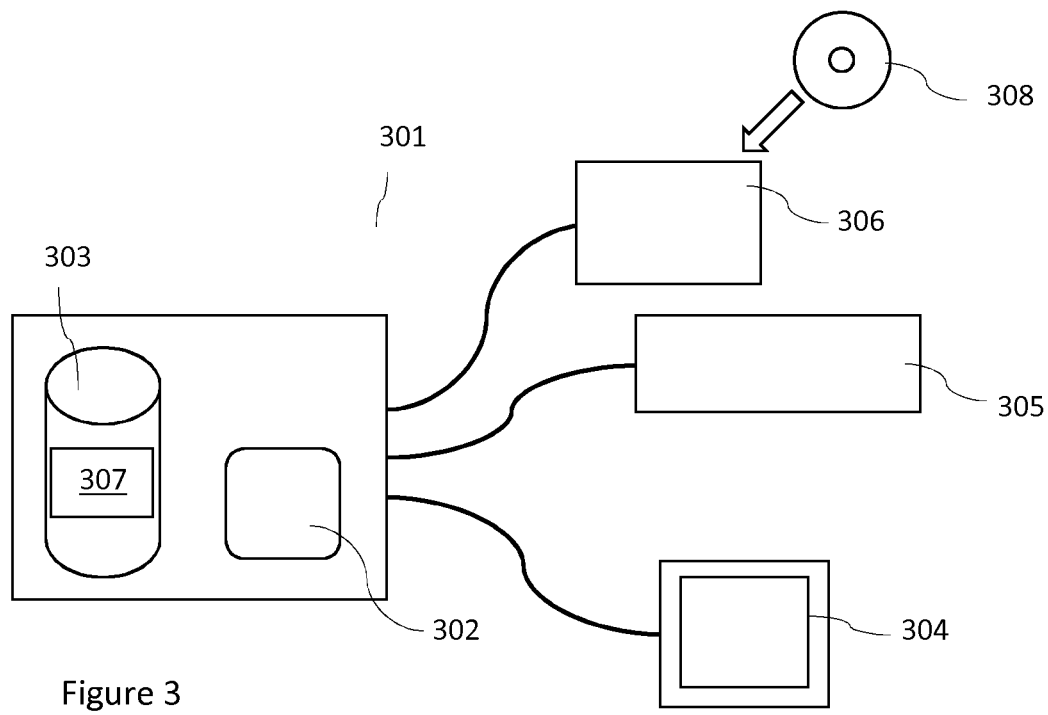
FIG. 3 is a schematic illustration of a computer system according to an example embodiment of the invention.

FIG. 3 schematically illustrates an example of a computer system 301 according to the invention. The system comprises a processor 302, coupled to a memory 303. Furthermore, the system can include a display device 304 (e.g. for displaying a graphical user interface, information related to different treatment plans and/or to scheduling of treatment plans for a plurality of patients, etc.), a data input device 305 (e.g. a keyboard, a mouse or any other suitable device for data input) and a data reading/writing device 306 (e.g. an optical drive, USB interface, or any other suitable device for reading/writing data). The processor 302 can be of any kind, such as one or more central processing units (CPU) or any kind of parallel processor system, e.g. based on one or more graphics processing units (GPU). The memory 303 can be any kind of volatile or non-volatile memory suitable for storing and retrieving information, such as, for example, a hard drive. The memory 303 has a computer program 307 stored thereon. The computer program 307 comprises computer-readable instructions for performing selection of at least one treatment plan where the computer-readable instructions can be transferred to, and executed by, the processor 302. When executed by the processor 302, the computer-readable instructions will perform a method as illustrated in FIG. 1 for retrieving alternative treatment plans for at least one patient and selecting a treatment plan for the at least one patient on the basis of plan quality, required resources and resource availability. A selected treatment plan and/or any other related information, such as any scheduling information related to the treatment plan, can be stored on the memory 303. The computer program 307 can also be stored on a non-transitory computer readable medium 308, e.g. a USB drive, an optical data carrier such as a CD-ROM, or any other suitable portable information storage device, so that the computer program 307 can be loaded to the memory 303 and/or transferred to different computing systems. The system described with reference to FIG. 3 is merely an example, and a computer system according to the invention does not necessarily comprise all the illustrated components, and/or might comprise other components not illustrated.

The invention has been described with reference to a number of example embodiments. It is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. In addition, it will be understood that features in one embodiment may be combined with features in other embodiments of the invention.

The invention claimed is:

1. A method for automatic selection of a radiotherapy treatment plan performed with a processor and comprising:
   providing a set comprising a plurality of alternative radiotherapy treatment plans for each of a plurality of patients, wherein each of the plurality of alternative radiotherapy treatment plans has a specified plan quality and requires a specified resource;
   formulating a constrained mixed integer optimization problem wherein a combined plan quality is to be optimized subject to constraints that the resources required for treatment may not exceed resource availability, the combined plan quality being defined as a total plan quality determined by selecting, for each of the plurality of patients, one radiotherapy treatment plan from the plurality of alternative radiotherapy treatment plans and combining the respective treatment plan qualities for the selected radiotherapy treatment plans;
   solving said optimization problem using an exact or heuristic optimization method;
   selecting from among the plurality of alternative radiotherapy treatment plans for each of the plurality of patients the one radiotherapy treatment plan per patient that optimizes the combined plan quality;
   scheduling the selected radiotherapy treatment plans that optimize the combined plan quality for delivery on the specified resource; and
   displaying on a graphical user interface of a display screen, for each specified resource, unavailable time slots and the selected radiotherapy treatment plans automatically scheduled in at least some available time slots.

2. The method according to claim 1, wherein one or more of said alternative radiotherapy treatment plans is an automatically determined treatment plan determined on the basis of a planned dose of another of said alternative radiotherapy treatment plans.

3. The method according to claim 1, wherein at least one or more of said alternative radiotherapy treatment plans is a combined plan based on a combination of two different radiotherapy treatment plans for one of the plurality of patients, wherein the plan quality of said combined plan is based on a combination of the plan qualities of said two different radiotherapy treatment plans.

4. The method according to claim 1, wherein the automatic selection of a radiotherapy treatment plan is partly based on a shortest possible time till delivery of treatment according to each of said alternative radiotherapy treatment plans.

5. The method according to claim 4, wherein the automatic selection of a radiotherapy treatment plan is performed partly on the basis of a patient priority reflecting the urgency for treatment of a patient.

6. A computer program product comprising computer-readable instructions which, when executed on a computer, causes the computer to perform a method comprising:
   providing a set comprising a plurality of alternative radiotherapy treatment plans for each of a plurality of patients, wherein each of the plurality of alternative radiotherapy treatment plans has a specified plan quality and requires a specified resource;
   formulating a constrained mixed integer optimization problem wherein a combined plan quality is to be optimized subject to constraints that the resources required for treatment may not exceed resource availability, the combined plan quality being defined as a total plan quality determined by selecting, for each of the plurality of patients, one radiotherapy treatment plan from the plurality of alternative radiotherapy treatment plans and combining the respective treatment plan qualities for the selected radiotherapy treatment plans;
   solving said optimization problem using an exact or heuristic optimization method;
   selecting from among the plurality of alternative radiotherapy treatment plans for each of the plurality of patients the one radiotherapy treatment plan per patient that optimizes the combined plan quality;
   scheduling the selected radiotherapy treatment plans that optimize the combined plan quality for delivery on the specified resource; and
   displaying on a graphical user interface of a display screen, for each specified resource, unavailable time slots and the selected radiotherapy treatment plans automatically scheduled in at least some available time slots.

7. A computer system comprising:
   a display screen comprising a graphical user interface for displaying scheduling information including unavailable time slots and available time slots; and
   a processor coupled to at least one memory having stored thereon a computer program comprising computer-readable instructions, said processor configured to, by executing said computer-readable instructions, perform a method comprising:
      providing a set comprising a plurality of alternative radiotherapy treatment plans for each of a plurality of patients, wherein each of the plurality of alternative radiotherapy treatment plans has a specified plan quality and requires a specified resource;
      formulating a constrained mixed integer optimization problem wherein a combined plan quality is to be maximized subject to constraints that the resources required for treatment may not exceed resource availability, the combined plan quality being defined as a total plan quality determined by selecting, for each of the plurality of patients, one radiotherapy treatment plan from the plurality of alternative radiotherapy treatment plans and combining the respective treatment plan qualities for the selected radiotherapy treatment plans;
      solving said optimization problem using an exact or heuristic optimization method;

selecting from among the plurality of alternative radiotherapy treatment plans for each of the plurality of patients the one radiotherapy treatment plan per patient that optimizes the combined plan quality;

scheduling the selected radiotherapy treatment plans that optimize the combined plan quality for delivery on the specified resource in at least some of the available time slots; and displaying on the graphical user interface, for each specified resource, unavailable time slots and the selected radiotherapy treatment plans automatically scheduled in the at least some of the available time slots.

* * * * *